(12) United States Patent
Suddaby

(10) Patent No.: US 6,840,944 B2
(45) Date of Patent: Jan. 11, 2005

(54) VERTEBRAL BODY END PLATE CUTTER

(76) Inventor: Loubert Suddaby, 76 Tanglewood Dr., Orchard Park, NY (US) 14127

( * ) Notice: Subject to any disclaimer, the term of this patent is extended or adjusted under 35 U.S.C. 154(b) by 99 days.

(21) Appl. No.: 10/151,039

(22) Filed: May 21, 2002

(65) Prior Publication Data

US 2003/0220645 A1 Nov. 27, 2003

(51) Int. Cl.[7] ............................ A61B 17/56; A61B 17/32
(52) U.S. Cl. ......................... 606/105; 606/79; 606/205; 606/53
(58) Field of Search .............................. 606/79, 80, 81, 606/82, 83, 84, 85, 105

(56) References Cited

U.S. PATENT DOCUMENTS

2003/0135217 A1 * 7/2003 Buttermann et al. .......... 606/79
2003/0225416 A1 * 12/2003 Bonvallet et al. ........... 606/105

* cited by examiner

Primary Examiner—Cary E. O'Connor
Assistant Examiner—Candice C. Stokes
(74) Attorney, Agent, or Firm—Shoemaker and Mattare

(57) ABSTRACT

Precision recesses are cut in the end plates of vertebral bodies by inserting into the disc space a cutter having a pair of shell elements provided with cutting edges shaped to match bone growth apertures in a selected prosthesis. The remainder of the end plates are left undisrupted, to maximize bearing strength while promoting bone growth at the apertures.

11 Claims, 4 Drawing Sheets

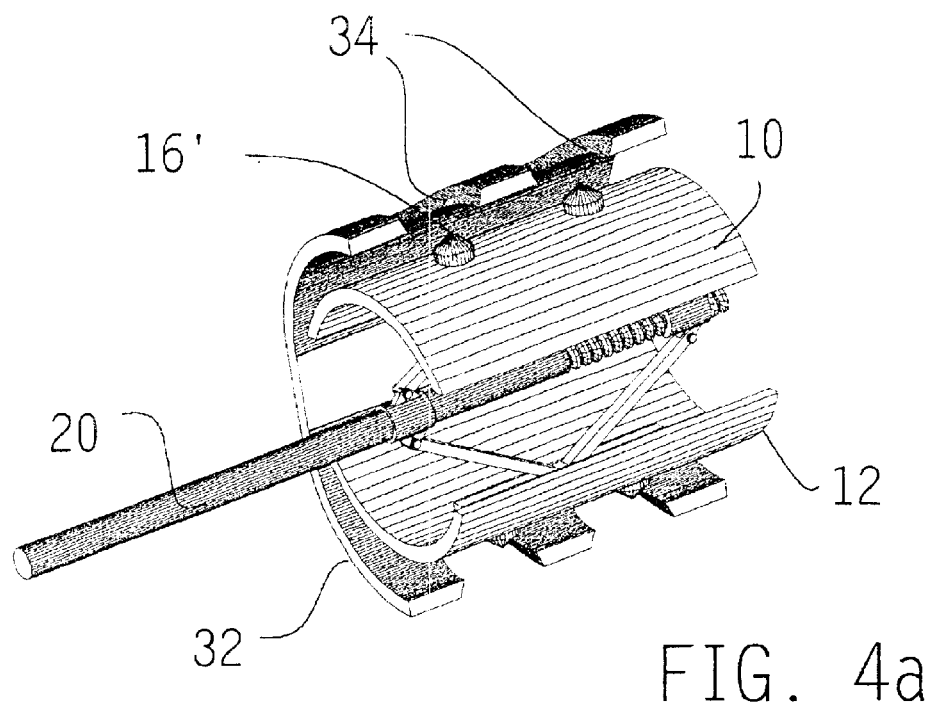
FIG. 4a
FIG. 4b
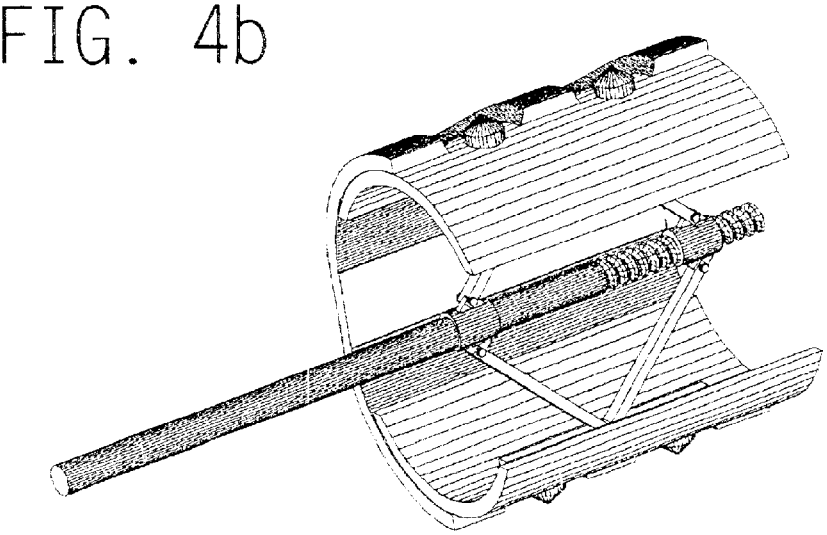

VERTEBRAL BODY END PLATE CUTTER

BACKGROUND OF THE INVENTION

This invention pertains to an implement suitable for the precise violation of vertebral body end plates during the performance of interbody spinal fusion techniques.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaption is a relatively recent change and as such has not benefitted from natural selection as much as have backbones held in the horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, and five in the low back or lumbar region. There are also five bones in the pelvis or sacral region which are normally fused together and form the back part of the pelvis. This column of bones is critical for protecting the delicate spinal cord and nerves, and for providing structural support for the entire body.

Between the vertebral bones themselves exist soft tissue structures—discs—composed of fibrous tissue and cartilage which are compressible and act as shock absorbers for sudden downward forces on the upright column. More importantly, the discs allow the bones to move independently of each other to permit functional mobility of the column of spinal vertebrae. Unfortunately, the repetitive forces which act on these intervertebral discs during repetitive day-to-day activities of bending, lifting and twisting cause them to break down or degenerate over time.

Presumably because of humans' upright posture, their intervertebral discs have a high propensity to degenerate. Overt trauma, or covert trauma occurring in the course of repetitive activities disproportionately affect more highly mobile areas of the spine. Disruption of a favorable for bony fusion to occur, the removal of end plate actually weakens the vertebral body making it more likely for the prosthesis itself to sink or subside into the adjacent soft cancellous bone of the adjacent vertebral bodies. If subsidence occurs, the stabilization provided by the prosthesis as regards adjacent vertebral elements is lost, and non-union can occur. Non-union or failure of the vertebral elements to fuse is obviously undesirable and in many instances leads to failure of the surgical procedure and a requirement for additional surgery.

While violation of the end plate is necessary to expose the inner cancellous bone to facilitate fusion, it is desirable to violate as little end plate as possible so that the remaining end plate can continue to provide structural support for the vertebral body thereby reducing or eliminating the chance of subsidence of the intervertebral prosthesis into the vertebral body itself.

It would be most desirable to disrupt end plate only over the portion of the prosthesis where vertebral cancerous bone would be exposed to bone graft material sequestered within the confines of the intervertebral prosthesis. This would allow the remaining intervening end plate to provide structural support to the vertebral body and provide a ready barrier to prevent prosthesis subsidence into the soft central cancellous bone of the vertebral body. Most present-day methods of implanting intervertebral prostheses require significant end plate disruption over the majority of the surface area of the prosthesis; subsidence of the implant not infrequently occurs.

To counteract this problem, it is desirable to disrupt or violate the vertebral body end plate exactly and exclusively at the apertures in the intervertebral prosthesis where cancerous bone and graft contact are to occur, thereby preserving end plate at all other areas of contact with the prosthesis. To achieve this idea of greater end plate support, precise end plate disruption limited only to the apertures allowing bone to graft contact must occur.

SUMMARY OF THE INVENTION

It is the object of this invention to provide an exact, limited and reliable method of end plate violation or disruption to facilitate vertebral interbody fusion. It is also intended that the device described herein be simple to manufacture and simple to use in daily clinical surgical disc's internal architecture leads to bulging, herniation or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal instability such as spinal curvature or lithesis.

The time-honored method of addressing the issues of neural irritation and instability resulting from severe disc damage have largely focused on removal of the damaged disc and fusing the adjacent vertebral elements together Removal of the disc relieves the mechanical and chemical irritation of neural elements, while osseous union (bone knitting) solves the problem of instability.

While cancerous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of bone or residual degrees of motion that retard or prohibit bony union. Intervertebral prosthesis in various forms have therefore been used to provide immediate stability and to protect and preserve an environment that fosters growth of grafted bone such that a structurally significant bony fusion can occur.

While intervertebral prostheses provide immediate stability, long term stability is dependent on a solid bony union between the vertebral body elements being fused. To achieve this, auto or allograft bone is grafted into the prosthesis to allow long term bony union to occur. The grafted bone, in turn, requires blood-borne nutrients to remain viable, or at least the graft must have intimate relationship to living bone so that the graft may be replaced or reconstituted through a process known as creeping substitution.

To achieve an intimate relationship between graft and vertebral bone, most prostheses have a variety of apertures allowing the juxtaposition of inner graft with outer adjacent vertebral bone.

In most instances the interbody space is prepared by drilling off or scraping the end plate such that exposed, bleeding cancellous bone is available for direct contact with the graft bone. While this situation is ideal for the bone graft in terms of preparing an environment practice with a variety or existing intervertebral prostheses already commercially available.

To achieve these objectives, two shells (having cutting edges conforming exactly to the size and shape of the apertures in the cranial and caudal components of the intervertebral fusion prosthesis) are distracted by a screw or lever mechanism such that end plate violation can be accomplished by a cookie cutter-like action.

BRIEF DESCRIPTION OF THE DRAWINGS

FIG. 4a shows an intervertebral prosthesis with a contracted vertebral endplate disrupter within.

FIG. 4b shows the end plate disrupter being distracted within an intervertebral prosthesis.

DESCRIPTION OF THE PREFERRED EMBODIMENT(S)

Figure 1:
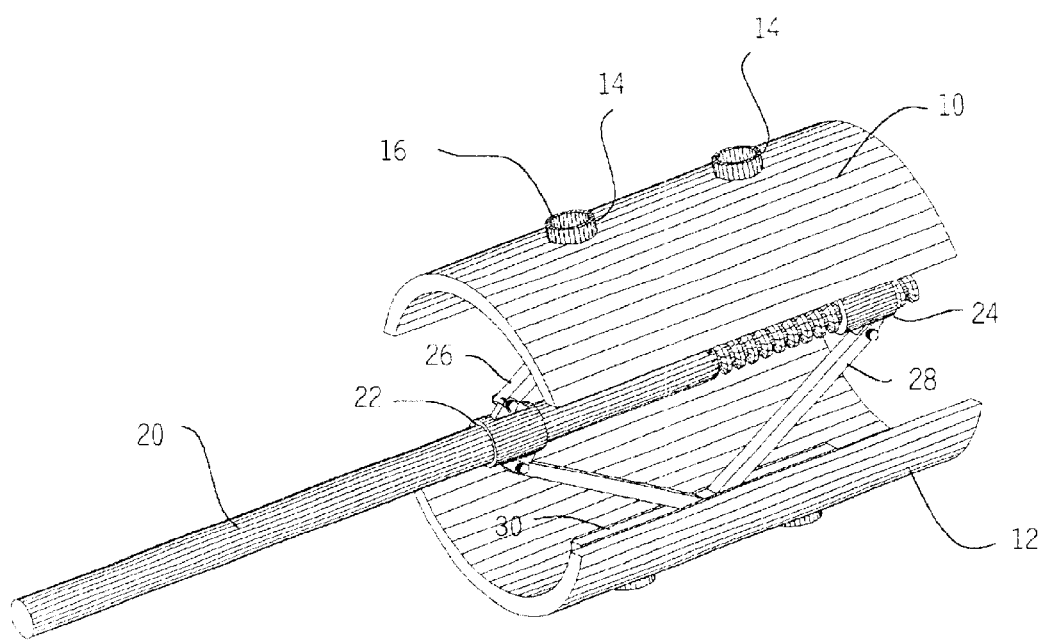
FIG. 1 illustrates an end plate disrupter with approximately circular (oblong or oval) cutting blades.
Figure 2:
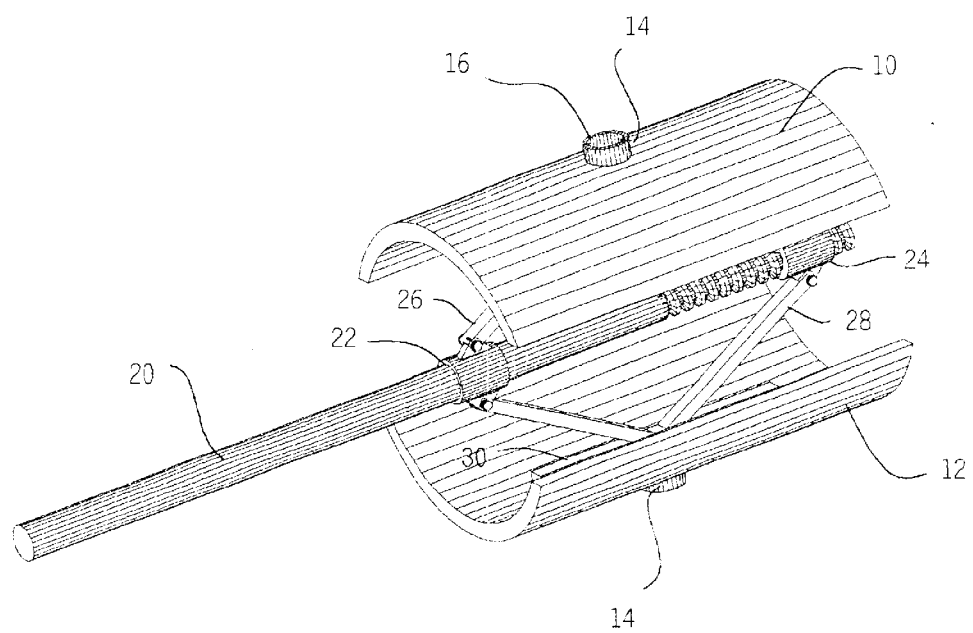
FIG. 2 illustrates an end plate disrupter with a single cutting blade suitable for an implant with a single aperture.
Figure 3:
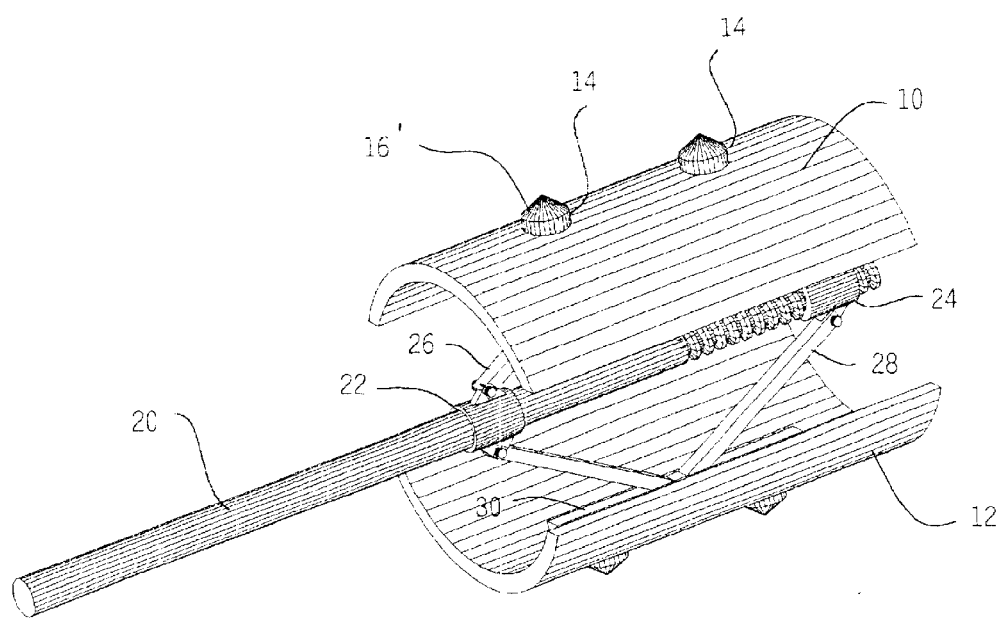
FIG. 3 illustrates and end plate disrupter with an angular point designed to fracture and invaginate the end plate as an alternative mechanism to circumscribed cutting as seen in FIGS. 1 and 2.

An end plate cutting tool suited for intervertebral fusion techniques includes at least two relatively movable elements such as the shells 10, 12 shown in FIGS. 1–3. Each of the shells has at least one (two in FIG. 1, one in FIG. 2) cutting structure 14 on its outer surface. In FIGS. 1 and 2, the cutting structure is a flange or band having a cutting edge 16 conforming in shape and location to bone growth apertures in cranial and caudal portions of a selected interbody fusion prosthesis 32 (shown in partial section in FIG. 4a).

The cutting structure 14 should be able to protrude 3–5 mm beyond the outer surface of the prosthesis, which has a wall thickness of 0.25–2.5 mm. So the design height of the cutting structure depends on the wall thickness of the prosthesis with which it is intended to be used.

The shells are supported on a jack screw mechanism including a shaft 20 threaded at its distal end, a fixed collar 22 seated in a groove knot shown) on the shaft, a traveling nut 24 engaged with the shaft threads, and a linkage comprising a first arm 26 connected to the collar, a second arm 28 connected to the nut, and a support arm 30. The outer ends of the first and second arms 24, 26 are pivotally interconnected at the center of the support arm. The shells 10, 12 are connected to respective support arms.

When the shells are expanded (compare FIGS. 4a and 4b) between adjacent vertebrae by turning the shaft clockwise, the cutting edges, protruding through the bone growth apertures 34 in the prosthesis, engage the end plates of the respective vertebrae. With the application of sufficient torque, the shells drive the cutting edges into the end plates, disrupting them in the shape of the bone growth windows of the prosthesis.

In operation, as the shells are slowly distracted within the prosthesis, the cutting mechanism protrudes through the apertures in the cranial and caudal component of the intervertebral prosthesis so that an precise cut out of the end plate occurs, exactly matching the size and shape of the aperture (s) in the prosthesis.

In the alternative illustrated in FIGS. 3 and 4, the cutting structure is a sharp point 16' designed to disrupt the end plate by fracturing it upward, thereby exposing the inner cancerous bone. This method of fracturing the end plate may be employed as an alternative to precise circumferential cutting, according to clinical or manufacturing desires.

Whatever the design of the cutting structure, once adequate end plate violation is deemed to have occurred, the shells are retracted and the implement is removed. The intervertebral prosthesis is then ready for application of bone graft while a maximum portion of the vertebral body end plate has been preserved to withstand compressive forces.

The advantages provided by this invention include:

The components of the tool are of simple design and manufacture.

The tool can be adapted for use with many existing intervertebral fusion implants.

The vertebral body end plates are violated with precision to facilitate intervertebral fusion.

The end plates are preserved to the greatest extent possible, to provide for greater stability of the implant and the prevention of undesirable implant subsidence.

End plate violation is more rapid, more accurate and more reliable than with techniques used heretofore.

Inasmuch as the invention is subject to variations and modifications, it is intended that the above description and the drawings shall be interpreted as merely illustrative of the invention defined by the following claims.

I claim:

1. A tool for precisely violating end plates of adjacent vertebral bodies for intervertebral fusion techniques, said tool comprising
    a first element for engaging one of said vertebral bodies,
    a second element for engaging the other of said vertebral bodies,
    at least one of said elements having at least one cutting structure thereon, and
    means for forcing said elements apart with sufficient force to drive said cutting structure into the end plate engaged thereby, so as to form a recess corresponding in shape to said cutting structure,
    wherein the forcing means is a screw jack.

2. The invention of claim 1, further comprising a lever mechanism for transmitting force from said screw jack to said elements.

3. A tool for precisely violating end plates of adjacent vertebral bodies for intervertebral fusion techniques, said tool comprising
    a first element for engaging one of said vertebral bodies,
    a second element for engaging the other of said vertebral bodies,
    at least one of said elements having at least one cutting structure thereon, and
    means for forcing said elements apart with sufficient force to drive said cutting structure into the end plate engaged thereby, so as to form a recess corresponding in shape to said cutting structure, wherein each of said elements is a shell having a protruding circumscribed cutting edge.

4. The invention of claim 3, wherein the cutting edges are of different shapes.

5. The invention of claim 3,
wherein each of the shells has at least one protruding point for interrupting and invaginating an end plate engaged thereby.

6. The invention of claim 5, wherein said point is conical.

7. The invention of claim 5, wherein said point is wedge-shaped.

8. The invention of claim 7, wherein said point is formed by the intersection of facets.

9. The invention of claim 3, wherein the shells can be both expanded and contracted between the vertebrae.

10. The invention of claim 3, wherein the shells can be both expanded and contracted within a vertebral interbody prosthesis.

11. The invention of claim 3, wherein the shells conform to the shape of bone growth apertures in an intervertebral fusion implant, such that the cutting edges or points protrude through the apertures of the implant sufficient to cause end plate disruption when said shells are distracted within the implant.

* * * * *